United States Patent
Foster et al.

(10) Patent No.: US 10,415,093 B2
(45) Date of Patent: Sep. 17, 2019

(54) METHOD FOR DIAGNOSING AND MONITORING INFLAMMATORY DISEASE PROGRESSION

(71) Applicant: MCMASTER UNIVERSITY, Hamilton (CA)

(72) Inventors: Warren Foster, Ancaster (CA); Nicholas Leyland, Hamilton (CA); Jocelyne Wessels, Guelph (CA); Sanjay Agarwal, Rancho Santa Fe, CA (US)

(73) Assignees: MCMASTER UNIVERSITY, Hamilton (CA); THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 15/094,086

(22) Filed: Apr. 8, 2016

(65) Prior Publication Data

US 2016/0281167 A1 Sep. 29, 2016

Related U.S. Application Data

(63) Continuation-in-part of application No. PCT/CA2014/000742, filed on Oct. 10, 2014.

(60) Provisional application No. 61/889,085, filed on Oct. 10, 2013.

(51) Int. Cl.
| | |
|---|---|
| *G01N 33/74* | (2006.01) |
| *G01N 33/53* | (2006.01) |
| *C12Q 1/6883* | (2018.01) |
| *C07K 16/22* | (2006.01) |
| *G01N 33/68* | (2006.01) |

(52) U.S. Cl.
CPC .......... *C12Q 1/6883* (2013.01); *C07K 16/22* (2013.01); *G01N 33/6893* (2013.01); *G01N 33/74* (2013.01); *C12Q 2600/106* (2013.01); *C12Q 2600/118* (2013.01); *C12Q 2600/158* (2013.01); *G01N 2333/475* (2013.01); *G01N 2333/71* (2013.01); *G01N 2800/364* (2013.01); *G01N 2800/52* (2013.01); *G01N 2800/7095* (2013.01)

(58) Field of Classification Search
None
See application file for complete search history.

(56) References Cited

U.S. PATENT DOCUMENTS

| | | | | |
|---|---|---|---|---|
| 2006/0173062 | A1* | 8/2006 | Boice | A61K 31/365 514/406 |
| 2010/0087464 | A1* | 4/2010 | Mi | C07D 403/14 514/275 |
| 2012/0220034 | A1* | 8/2012 | Ahlfors | C12N 5/0618 435/375 |

OTHER PUBLICATIONS

Desmet et al, Cell. Mol. Life Sci. 63 (7-8), 755 (2006).*
Biological Science, 2nd ed., W.T. Keeton, W.W. Norton & Co., Inc. 1972, pp. 250-251.*
Borghese, et al. (2010) Gynecol Obstet Fertil. Jul.-Aug.; 38(7-8):442-6.
Browne, et al. (2012) Fertil Steril. Sep.; 98(3):713-9.
Giannini, et al. (2010) J Endometr Pelvic Pain Disord 2(3): 144-150.

* cited by examiner

*Primary Examiner* — James Martinell
(74) *Attorney, Agent, or Firm* — Milstein Zhang & Wu LLC

(57) ABSTRACT

Methods for diagnosing or monitoring endometriosis in a mammal are provided. The methods include the steps of determining the expression levels of BDNF and its receptor, Ntrk2, in a biological sample from the mammal, and determining that the mammal has endometriosis when the BDNF and Ntrk2 expression levels in the sample are elevated.

11 Claims, 10 Drawing Sheets
Specification includes a Sequence Listing.

Circulating BDNF in Women With and Without Endometriosis

Plasma BDNF in Cases

Relationship between Circulating BDNF Concentrations and Pain in Women with Untreated Endometriosis

```
 1 AVDMSGGTVT VLEKVPVSKG QLKQYFYETK CNPMGYTKEG CRGIDKRHWN SQCRTTQSYV
61 RALTMDSKKR IG (SEQ ID NO:1)
```

B

```
 1 AVDMSGGTVT VLEKVPVSKG QLKQYFYETK CNPMGYTKEG CRGIDKRHWN SQCRTTQSYV
61 RALTMDSKKR IG (SEQ ID NO:1)
```

C

```
 1 AVDMSGGTVT VLEKVPVSKG QLKQYFYETK CNPMGYTKEG CRGIDKRHWN SQCRTTQSYV
61 RALTMDSKKR IG (SEQ ID NO:1)
```

D

```
 1 SITLSCSVAG DPVPNMYWDV GNLVSKHMNE TSHTQGSLRI TNISSDDSGK QISCVAENLV
61 GEDQDSVNLT (SEQ ID NO:2)
```

E

```
 1 KSVTLSCSVG GDPLPTLYWD VGNLVSKHMN ETSHTQGSLR ITNISSDDSG KQISCVAENL
61 VGEDQDSVNL T (SEQ ID NO:3)
```

F

```
 1 SVTISCSVGG DPLPTLYWDV GNLVSKHMNE TSHTQGSLRI TNISSDDSGK QISCVAENLV
61 GEDQDSVNLT (SEQ ID NO:4)
```

```
  1 tgcagtggac atgtcgggcg ggacggtcac agtccttgaa aaggtccctg tatcaaaagg
 61 ccaactgaag caatacttct acgagaccaa gtgcaatccc atgggttaca caaaagaagg
121 ctgcaggggc atagacaaaa ggcattggaa ctcccagtgc cgaactaccc agtcgtacgt
181 gcgggccctt accatggata gcaaaaagag aattggctg (SEQ ID NO:5)
```

B

```
  1 tgcagtggac atgtctggcg ggacggtcac agtcctagag aaagtcccgg tatccaaagg
 61 ccaactgaag cagtatttct acgagaccaa gtgtaatccc atgggttaca ccaaggaagg
121 ctgcaggggc atagacaaaa ggcactggaa ctcgcaatgc cgaactaccc aatcgtatgt
181 tcgggccctt actatggata gcaaaaagag aattgg (SEQ ID NO:6)
```

C

```
  1 tgcagtggac atgtccggtg ggacggtcac agtcctggag aaagtcccgg tatcaaaagg
 61 ccaactgaag caatatttct acgagaccaa gtgtaatccc atgggttaca cgaaggaagg
121 ctgcaggggc atagacaaaa ggcactggaa ctcgcaatgc cgaactaccc aatcgtatgt
181 tcgggccctt actatggata gcaaaaagag aattggctg (SEQ ID NO:7)
```

D

```
  1 gtctatcaca ttatcctgta gtgtggcagg tgatccggtt cctaatatgt attgggatgt
 61 tggtaacctg gtttccaaac atatgaatga aacaagccac acacagggct ccttaaggat
121 aactaacatt tcatccgatg acagtgggaa gcagatctct tgtgtggcgg aaaatcttgt
181 aggagaagat caagattctg tcaacctcac (SEQ ID NO:8)
```

E

```
  1 tgcagtggac atgtctggcg ggacggtcac agtcctagag aaagtcccgg tatccaaagg
 61 ccaactgaag cagtatttct acgagaccaa gtgtaatccc atgggttaca ccaaggaagg
121 ctgcaggggc atagacaaaa ggcactggaa ctcgcaatgc cgaactaccc aatcgtatgt
181 tcgggccctt actatggata gcaaaaagag aattgg (SEQ ID NO:6)
```

F

```
  1 tgcagtggac atgtccggtg ggacggtcac agtcctggag aaagtcccgg tatcaaaagg
 61 ccaactgaag caatatttct acgagaccaa gtgtaatccc atgggttaca cgaaggaagg
121 ctgcaggggc atagacaaaa ggcactggaa ctcgcaatgc cgaactaccc aatcgtatgt
181 tcgggccctt actatggata gcaaaaagag aattggctg (SEQ ID NO:7)
```

METHOD FOR DIAGNOSING AND MONITORING INFLAMMATORY DISEASE PROGRESSION

PRIORITY CLAIMS AND RELATED PATENT APPLICATIONS

This application claims the benefit of priority, under 35 U.S.C. § 120, from the US designation of International Application No. PCT/CA2014/000742, filed on Oct. 10, 2014, which claims benefit of priority from U.S. Provisional Application Ser. No. 61/889,085, filed on Oct. 10, 2013, the entire content of each of which is incorporated herein by reference in its entirety for all purposes.

FIELD OF THE INVENTION

The present invention provides compositions and/or methods for diagnosis or assessment of progression of inflammatory diseases, in particular, endometriosis.

BACKGROUND OF THE INVENTION

Neurotrophins are a family of soluble, small molecular weight proteins that act in the nervous system to promote neuronal development, differentiation, growth, and maintenance. The neurotrophin signalling network is complex. Neurotrophins can be translated as pro-proteins and cleaved into their active forms, or they can induce signalling cascades in their pro-form. Generally, the two forms have opposing functions. The neurotrophin family comprises four ligands, brain-derived neurotrophic factor (BDNF), nerve growth factor (NGF), neurotrophin 3 (NTF3), and neurotrophin 4 (NTF4), and four receptors: neurotrophic tyrosine receptor kinase (NTRK) 1, NTRK2, NTRK3, and the nerve growth factor receptor (NGFR). Although all four neurotrophins bind to NGFR with similar affinities, and their pro-protein forms have been shown to bind to this receptor as well, they are more selective in binding the NTRKs. NGF binds to NTRK1, BDNF and NTF4 bind to NTRK2, and NTF3 binds to NTRK3, each with high affinity. Another lesser known neurotrophin co-receptor, sortilin (SORT1), has been shown to interact with pro-neurotrophins in the brain and to control their release in either a constituent or activity-dependent manner. SORT1 is also involved in an elaborate intracellular trafficking network directing proteins to various fates: cell surface expression, secretion, endocytosis, or transport within the cell. However, the regulation and expression of this complex signalling network in the uterus remains unexplored.

Although mainly recognized for their supportive function within the nervous system, BDNF and its high affinity receptor NTRK2 have been shown to participate in ovarian development, follicular development, oocyte survival, endometrial stem cell neurogenesis, and normal placental development. The interaction between BDNF and NTRK2 is not only capable of inducing neuronal development, differentiation, growth, and maintenance; activation of the BDNF-NTRK2 pathway has been demonstrated to induce angiogenesis, cellular proliferation, adhesion, and resistance to apoptosis. Each of these pathways is inextricably linked to reproduction, however the mechanisms regulating the uterine expression of BDNF, NTRK2, NGFR, and SORT1 remain unknown.

Thus, it would be desirable to better understand neurotrophin regulation in the mammalian uterus, and to develop methods to recognize one or more pathologies associated with a neurotrophin.

SUMMARY OF THE INVENTION

It has now been determined that elevated expression levels of BDNF and full-length Ntrk2 receptor in a biological sample from a mammal is indicative of endometriosis.

Thus, in one aspect a method of diagnosing endometriosis in a mammal is provided comprising the steps of: determining the expression level of BDNF in a biological sample from the mammal and comparing the BDNF level to a control BDNF level; determining the expression level of full-length Ntrk2 in the biological sample and comparing the Ntrk2 level to a control Ntrk2 level; and diagnosing the mammal with endometriosis when the BDNF level and Ntrk2 level are both elevated by at least 10% as compared with the control levels.

In another aspect, a method of monitoring a mammal following treatment for endometriosis comprising: determining the expression level of BDNF in a biological sample from the mammal and comparing the level to a pre-treatment BDNF level, and determining that the mammal is responding to treatment if the BDNF level is reduced by at least 10% as compared to the pretreatment BDNF level.

In a further aspect of the invention, a kit is provided comprising a BDNF-specific reactant, a full-length Ntrk2-specific reactant, and, optionally, instructions for use to detect endometriosis in a mammal.

In a further aspect, a method of diagnosing inflammatory disease in a mammal is provided. The method comprises determining the expression level of BDNF in a biological sample from the mammal and comparing the BDNF level to a control BDNF level to determine if the BDNF level is elevated in comparison to the BDNF baseline level, wherein an elevated BDNF level is indicative of inflammatory disease in the mammal.

These and other aspects of the invention are described herein by reference to the description and figures as follows.

BRIEF DESCRIPTION OF THE FIGURES

FIG. 9 illustrates the amino acid sequences of human (A), mouse (B) and rat (C) mBDNF, and of human (D), mouse (E) and rat (F) full-length Ntrk2; and FIG. 10 illustrates the nucleic acid sequence of human (A), mouse (B) and rat (C) BDNF transcripts, and human (D), mouse (E) and rat (F) Ntrk2 transcripts.

DETAILED DESCRIPTION OF THE INVENTION

Figure 1:
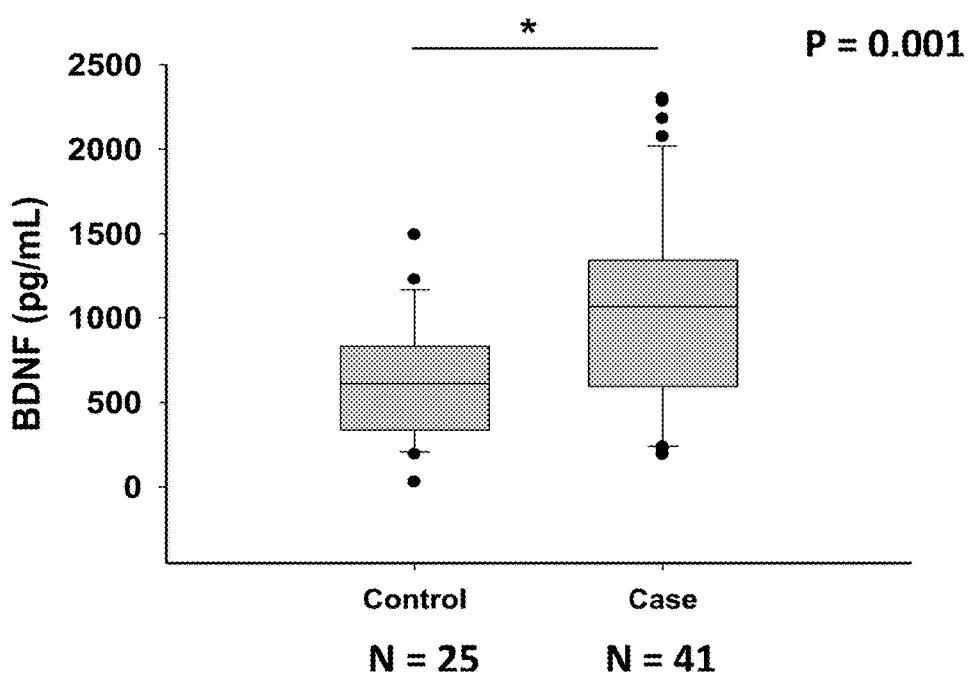
FIG. 1 graphically illustrates that circulating concentration of BDNF is higher in the plasma of women with endometriosis vs. a control population.

A method of diagnosing endometriosis in a mammal is provided comprising the steps of: determining the expression level of BDNF in a biological sample from the mammal and comparing the level to a control BDNF baseline level; determining the expression level of full-length Ntrk2 in the biological sample from the mammal and comparing the Ntrk2 level to a control Ntrk2 baseline level; diagnosing the mammal with endometriosis when the BDNF level and Ntrk2 level are both elevated by at least 10% as compared with their baseline levels.

Brain-derived neurotrophic factor, referred to herein as BDNF, is a secreted protein that supports growth and survival of neurons. As used herein, BDNF encompasses mammalian BDNF, including human and functionally equivalent variants thereof such as non-human BDNF, and isoforms or other variants of human and non-human BDNF, including pro-BDNF and mBDNF. Functionally equivalent BDNF variants are variants that incorporate alterations, such as, but not limited to, amino acid deletions, additions or substitutions, which do not significantly adversely affect BDNF activity. Post-translationally modified BNDF is referred to as mature BDNF or mBDNF. Amino acid sequences for mBDNF are known and readily accessible at sequence databases, such as GenBank, by reference to nucleotide accession nos., e.g. human mBDNF (accession no. KC855559), mouse mBDNF (accession no. KC855560), rat mBDNF (accession no. KC855561), pig mBDNF (accession no. KC855563) and horse mBDNF (accession no. KC855562). mBDNF amino acid sequences are illustrated in FIG. 9, and nucleic acid encoding sequences are shown in FIG. 10.

Neurotrophic tyrosine kinase, receptor, type 2 (Ntrk2), also known as TrkB receptor, TrkB tyrosine kinase or BDNF/NT-3 growth factor receptor, is a BDNF receptor. As used herein, Ntrk2 encompasses full-length mammalian Ntrk2, including human and functionally equivalent variants thereof such as non-human Ntrk2. Functionally equivalent variants of full-length Ntrk2 encompass full-length Ntrk2 which may incorporate alterations, such as, but not limited to, minor amino acid alternations such as deletions, additions or substitutions, e.g. involving 1 or 2 amino acid residues, which do not significantly adversely affect Ntrk2 activity, such as BDNF binding. Amino acid sequences of various forms of full-length Ntrk2 are known and readily accessible at sequence databases, such as GenBank, by reference to nucleotide accession nos., e.g. human Ntrk2 (KC855566), mouse Ntrk2 (KC855567), rat Ntrk2 (KC855568) and horse Ntrk2 (KC855569). Ntkr2 amino acid sequences are illustrated in FIG. 9, and nucleic acid encoding sequences are shown in FIG. 10.

To conduct the present method, a BDNF- and Ntrk2-containing biological sample(s) is obtained from a female mammal. The term "biological sample" is meant to encompass any mammalian fluid or tissue sample that may contain nucleic acid encoding the target BDNF and Ntrk2 gene, or that may contain the target BDNF and Ntrk2 protein. Suitable biological samples include, for example, blood (including menses), serum, plasma, urine, peritoneal fluid or biopsied endometrial tissue. Any of these samples may be obtained from the mammal in a manner well-established in the art. The term "mammal" is used herein to refer to both human and non-human mammals including domestic animals, e.g. cats, dogs and the like, livestock and undomesticated animals.

Once a suitable BDNF-containing and Ntrk2-containing biological sample is obtained, it is analyzed to determine the expression level of BDNF and full-length Ntrk2 in the sample, either transcript level or protein concentration. As one of skill in the art will appreciate, the expression level of each biomarker may be determined using one of several techniques established in the art, including methods of quantifying nucleic acid encoding the target biomarker, such as PCR-based techniques, microarrays, gene expression system, and Northern or Southern blotting techniques, or methods of quantifying protein biomarker, such as immunological or activity assay, Western blotting, or mass spectrometry. With respect to BDNF, it is the level of mBDNF that is related to endometriosis; however, total BDNF does reflect changes in mBDNF. Thus, depending on the biological sample used, either the expression level of total BDNF may be determined, or, if possible in the sample obtained, the expression level of mBDNF may be specifically determined.

In one embodiment, the expression level of BDNF and Ntrk2 in a biological sample from a mammal may be determined based on the levels of nucleic acid (i.e. DNA or mRNA transcript) encoding the target protein biomarker in the biological sample. Methods of determining DNA or mRNA levels are known in the art, and include, for example, PCR-based techniques (such as RT-PCR), and Northern or Southern blotting techniques which generally include the application of gel electrophoresis to isolate the target nucleic acid, followed by hybridization with specific labeled probes. Probes for use in these methods can be readily designed based on the known sequences of genes encoding the protein biomarker, as well as the known amino acid sequence of the target biomarker, and may comprise about 15-40 nucleotides, for example, 20-35 nucleotides. Probes that target mBDNF are generally suitable for use in the present method. Such probes would detect total BDNF in a sample. For Ntrk2, probes that target full-length Nkrt2 are generally suitable to detect Ntrk2. Example BDNF probes include GAGCTGAGCGTGTGTGACAG (forward) (SEQ ID NO: 9) and CTTATGAATCGCCAGCCAAT (reverse) (SEQ ID NO: 10), and example Ntrk2 probes include CAATTGTGGTTTGCCATCTG (forward) (SEQ ID NO: 11) and TGCAAAATGCACAGTGAGGT (reverse) (SEQ ID NO: 12). Suitable labels for use are well-known, and include, for example, fluorescent, chemiluminescent and radioactive labels.

A preferred assay method to measure biomarker transcript abundance includes using the NanoString nCounter gene expression system. The system utilizes a pair of probes, namely, a capture probe and a reporter probe, each comprising a 35- to 50-base sequence complementary to the biomarker transcript. The capture probe additionally includes a short common sequence coupled to an immobilization tag, e.g. an affinity tag that allows the complex to be immobilized for data collection. The reporter probe additionally includes a detectable signal or label, e.g. is coupled to a color-coded tag. Following hybridization, excess probes are removed from the sample, and hybridized probe/target complexes are aligned and immobilized via the affinity or other tag in a cartridge. The samples are then analyzed, for example using a digital analyzer or other processor adapted for this purpose. Generally, the color-coded tag on each transcript is counted and tabulated for each target transcript to yield the expression level of each transcript on the sample.

In other embodiments, the expression level of protein, mBDNF and full-length Ntrk2, in a sample may be measured by immunoassay using an antibody specific to the target protein. As above, the antibody is bound to the target protein and bound antibody is quantified by measuring a detectable marker which may be linked to the antibody or other component of the assay, or which may be generated during the assay. Detectable markers may include radioactive, fluorescent, phosphorescent and luminescent (e.g. chemiluminescent or bioluminescent) compounds, dyes, particles such as colloidal gold and enzyme labels.

The term "antibody" is used herein to refer to monoclonal or polyclonal antibodies, or antigen-binding fragments thereof, e.g. an antibody fragment that retains specific binding affinity for the target biomarker. Antibodies to the target biomarkers are generally commercially available. For example, BDNF antibodies to various BDNF immunogens, including internal, and N- and C-terminal, are commercially available, for example, from Sigma Alderich, Santa Cruz Biotech and AbCam, while Nkrt2 antibodies are commercially available from, for example, AbCam, R&D Systems and Origene Technologies. As one of skill in the art will appreciate, antibodies to the target proteins may also be raised using techniques conventional in the art. For example, antibodies may be made by injecting a host animal, e.g. a mouse or rabbit, with the antigen (target protein or immunogenic fragment thereof), and then isolating antibody from a biological sample taken from the host animal.

Different types of immunoassay may be used to determine expression level of target proteins, including indirect immunoassay in which the protein is non-specifically immobilized on a surface; sandwich immunoassay in which the protein is specifically immobilized on a surface by linkage to a capture antibody bound to the surface; competitive binding immunoassay in which a sample is first combined with a known quantity of antibody to bind the target protein in the sample, and then the sample is exposed to immobilized target protein which competes with the sample to bind any unbound antibody. To the immobilized protein/antibody is added a detectably-labeled secondary antibody that detects the amount of immobilized primary antibody, thereby revealing the inverse of the amount of target protein in the sample.

A preferred immunoassay for use to determine expression levels of target protein in a sample is an ELISA (Enzyme Linked ImmunoSorbent Assay) or Enzyme ImmunoAssay (EIA). To determine the level or concentration of the target protein using ELISA, the target to be analyzed is generally immobilized, for example, on a solid adherent support, such as a microtiter plate, polystyrene beads, nitrocellulose, cellulose acetate, glass fibers and other suitable porous polymers, which is pretreated with an appropriate ligand for the target, and then complexed with a specific reactant or ligand such as an antibody which is itself linked (either before or following formation of the complex) to an indicator, such as an enzyme. Detection may then be accomplished by incubating this enzyme-complex with a substrate for the enzyme that yields a detectable product. The indicator may be linked directly to the reactant (e.g. antibody) or may be linked via another entity, such as a secondary antibody that recognizes the first or primary antibody. Alternatively, the linker may be a protein such as streptavidin if the primary antibody is biotin-labeled. Examples of suitable enzymes for use as an indicator include, but are not limited to, horseradish peroxidase (HRP), alkaline phosphatase (AP), β-galactosidase, acetylcholinesterase and catalase. A large selection of substrates is available for performing the ELISA with these indicator enzymes. As one of skill in the art will appreciate, the substrate will vary with the enzyme utilized. Useful substrates also depend on the level of detection required and the detection instrumentation used, e.g. spectrophotometer, fluorometer or luminometer. Substrates for HRP include 3,3',5,5'-Tetramethylbenzidine (TMB), 3,3'-Diaminobenzidine (DAB) and 2,2'-azino-bis(3-ethylbenzothiazoline-6-sulphonic acid) (ABTS). Substrates for AP include para-Nitrophenylphosphates. Substrates for β-galactosidase include β-galactosides; the substrate for acetylcholinesterase is acetylcholine, and the substrate for catalase is hydrogen peroxide.

As will be appreciated by one of skill in the art, assay methods which target the activity of a target protein may also be utilized to determine the expression level thereof in a sample. In this regard, suitable assays would be known to the skilled person, including for example, a mBDNF-Nkrt2 binding assay.

The expression level of mBDNF and Nkrt2 in a given sample may be analyzed individually or together using, for example, biochip array technology. Generally, biochip arrays provide a means to simultaneously determine the level of multiple biomarkers in a given sample. These arrays may utilize ELISA technology and, thus, the biochip may be modified to incorporate capture antibodies for each target at pre-defined sites on the surface.

Once the expression level of BDNF and full-lengthNtrk2 in a biological sample of a mammal have been determined, these expression levels are compared to control expression levels, i.e. the expression level of BDNF and Ntrk2 in a healthy control, i.e. a mammal that does not have endometriosis. Alternatively, the level of each of BDNF and Ntrk2 may be compared to the expression level of a "housekeeping gene". The term "housekeeping gene" as used herein is meant to refer to a gene that encodes a protein product that is not connected to, involved in or required for processes specific to endometriosis, and thus, exhibits a fixed expression level in mammals with and without endometriosis. Examples of suitable housekeeping genes include, but are not limited to, genes encoding ACTB (Beta-actin), GAPDH (Glyceraldehyde 3-phosphate dehydrogenase), RPLP0 (60S acidic ribosomal protein P0), GUSB (beta-glucuronidase), and TFRC (transferring receptor 1). In a comparison of the expression levels of target biomarkers to housekeeping genes, a determination of an increase in transcript abundance or expression of mBDNF and Ntrk2 is indicative of endometriosis.

The level of expression that would be considered to represent an increased or elevated expression level of BDNF and Ntrk2 that is indicative of endometriosis in accordance with the present method may be determined relative to BDNF and Ntrk2 levels in a healthy control sample, or relative to the expression of one or more housekeeping genes. Generally, a reproduceable statistically significant increase in the expression of a biomarker, for example, an increase of at least about 5%, preferably, at least about 10%, 20%, 30%, 40% or 50% or greater, in comparison to the expression levels in a control, or in comparison to the expression level of a housekeeping gene, is considered to be elevated expression that is relevant with respect to a diagnosis of endometriosis. Generally, a plasma BDNF level in the range of about 100-500 pg/ml is considered to be normal, while plasma BDNF levels higher than this, e.g. about 10-50% or greater, are indicative of endometriosis, e.g. for example, plasma BDNF levels of 800 pg/ml or greater are indicative of endometriosis. As one of skill in the art will appreciate, the difference in the level of biomarker expression as compared to expression of the housekeeping gene(s) may vary with the methodology employed to quantify and analyse nucleic acid and/or protein expression.

In another aspect, a method to monitor mammal response to treatment for endometriosis, including surgical or drug therapy (e.g. hormone therapy), is also provided. The method of monitoring a mammal following treatment of endometriosis comprises: determining the expression level of BDNF in a BDNF sample from the mammal and comparing the level to a pre-treatment BDNF expression level to determine if the BDNF level has decreased in comparison to the pre-treatment BDNF level. A significant decrease, i.e. a decrease of at least about 10% or greater, preferably at least about 20% or greater, e.g. 30-50% or greater in the BDNF level compared to the pre-treatment level indicates that the mammal is responding to the treatment.

Disease recurrence may also be monitored in a mammal previously successfully treated for endometriosis using a method in accordance with the invention. A method as used to diagnose endometriosis in a first instance would be applicable. In particular, BDNF expression levels, either total BDNF or mBDNF, and Ntrk2 expression levels are determined in a relevant biological sample from the mammal as described. It is then determined whether or the BDNF and Ntrk2 levels represent a significant increase in comparison to a control value, or in comparison to the level of a selected housekeeping gene, wherein a significant increase (e.g. 10-50% or greater) is indicative of disease recurrence.

In a further embodiment of the invention, a kit is provided comprising an mBDNF-specific reactant, a full-length Ntrk2-specific reactant, and optionally, instructions for use in methods of diagnosing and/or monitoring disease recurrence, disease progression or treatment of endometriosis in a mammal. BDNF- and Ntrk2-specific reactants may include nucleic acid probes or antibodies based on the known nucleic acid and amino acid sequences of BDNF and Ntrk2. A substrate for BDNF and/or Ntrk2 may also be used as a reactant. The reactants may be associated with an indicator (e.g. an enzyme, such as horseradish peroxidase (HRP), alkaline phosphatase (AP), β-galactosidase, acetylcholinesterase and catalase) such that the interaction of the reactant with BDNF and Ntrk2 yields a product or signal, releases the enzyme that is readily detectable and indicative of BDNF and Ntrk2 in the biological sample.

The kit may be provided in the form of a biochip which incorporates a BDNF-specific reactant (or mBDNF reactant) and/or a full-length Ntrk2-specific reactant at pre-defined sites on the surface thereof. The reactants are each associated with an indicator such that in the presence of BDNF and Ntrk2, a detectable product or signal is released, as above. The biochip may be adapted for use with a blood sample, e.g. from a finger prick, or a menses sample.

In another embodiment, a biochip adapted for the electrochemical detection of circulating BDNF is provided. A BDNF-specific reactant, such as an antibody, and optionally, an Ntrk2-specific reactant, is bonded to circuits, e.g. an electrode, in a silicone microchip. When BDNF from a sample binds to the BDNF reactant, it alters the voltage potential measured across the probe resulting in a measurable electrical output that is detectable by transducers in the device and which is proportional to the concentration of BDNF in the sample.

Measurement of plasma concentrations of total and/or mBDNF is potentially valuable as a method to measure non-specific inflammation in a mammal that may be useful to prompt further investigation into the cause thereof. Thus, in another aspect, a method of diagnosing inflammation-causing disease in a mammal is provided. The method comprises determining the level of BDNF in a BDNF sample from the mammal and comparing the level to a control BDNF baseline level to determine if the BDNF level is elevated in comparison to the BDNF baseline level, wherein an elevated BDNF level is indicative of inflammation-causing disease in the mammal. Inflammation-causing disease may include, for example, cancer such as ovarian cancer and other endocrine tumors, lupus, Crohn's disease, ulcerative colitis, polycystic ovarian syndrome and periodontal disease.

Embodiments of the invention are described by reference to the following specific examples which are not to be construed as limiting.

Example 1—BDNF Determination by Immunoassay

Materials and Methods

Study Participants.

Women undergoing surgery for endometriosis (cases, N=76) or other benign gynaecological surgeries (symptomatic controls, N=20) were recruited prospectively. Women with no history of pelvic pain, who were not undergoing surgery were also recruited (asymptomatic controls, N=18). Study participants completed demographics and gynecological history questionnaires. Menstrual cycle length, date of last menstruation, and pelvic pain assessed on a 5 question, 5-point visual analog scale was recorded for each participant. Women who underwent laparoscopic surgery were categorized as a case or symptomatic control by a gynaecological surgeon, and the diagnoses were later confirmed with pathology reports. The stage of endometriosis was determined during surgery according to the revised Classification of the American Society of Reproductive Medicine [33]. All study participants completed written informed consents and the study was approved by the Hamilton Health Sciences Integrated Research Ethics Board, McMaster University (IRB#06-064, and 12-083-T).

A trained research nurse collected peripheral blood from the cubital vein from each participant in plasma separator tubes (BD Canada, Mississauga, ON, Canada). Blood was placed on ice, transported to the laboratory, and processed according to established Standard Operating Procedures (SOPs: MAC-OG-RBF-001 to MAC-OG-RBF-006). Immediately after plasma separation, plasma was divided into 1.8 mL cryovials (Sigma-Aldrich Chemical Company, St. Louis. Mo.) and frozen at −80° C. until required for assay.

Exclusions.

Individuals unable to provide consent, or under the age of 18 were excluded from the study. Women were also excluded from the study if they had a diagnosis of adenomyosis (4.4%), polycystic ovary syndrome (0.9%), or if the pathological findings did not correlate with the clinical impression (4.4%). Plasma samples were excluded from the study if they were hemolyzed (13.2%).

BDNF Assay.

Plasma samples were thawed at room temperature and circulating BDNF was quantified in triplicate using the BDNF Emax immunoassay ELISA (Promega, Madison, Wis., USA), following the manufacturer's protocol. Briefly, 96 well NUNC maxisorp plates were coated with anti-human BDNF antibody (provided with the kit) overnight. They were blocked the following morning using the block and sample buffer provided in the kit. Freshly thawed plasma samples were diluted 1:10 with sample buffer provided in the kit. Following the BDNF ELISA, the absorbance was read at 450 nm within 30 minutes using the Biotek Synergy spectrophotometer (Fisher Scientific, Ottawa, ON, Canada). BDNF concentration and % CV of the triplicates were calculated by the Biotek Synergy software.

Data and Statistical Analysis.

The intra-sample variation (triplicates) did not exceed 15% (% CV<15) in any plasma sample. A Grubb's test (http://graphpad.com/quickcalcs/Grubbs1.cfm) was used to identify statistical outliers (2.6%) which were omitted from analysis and values found to be non-detectable by ELISA (1.8%). Data were compared by t-test, one-way ANOVA, or linear regression (SigmaStat 3.5 Systat Software Inc., Chicago, Ill., USA). A P value of <0.05 was considered significant. Data are presented as box plot with lines representing the $25^{th}$, $50^{th}$, and $75^{th}$ percentiles.

Figure 2:
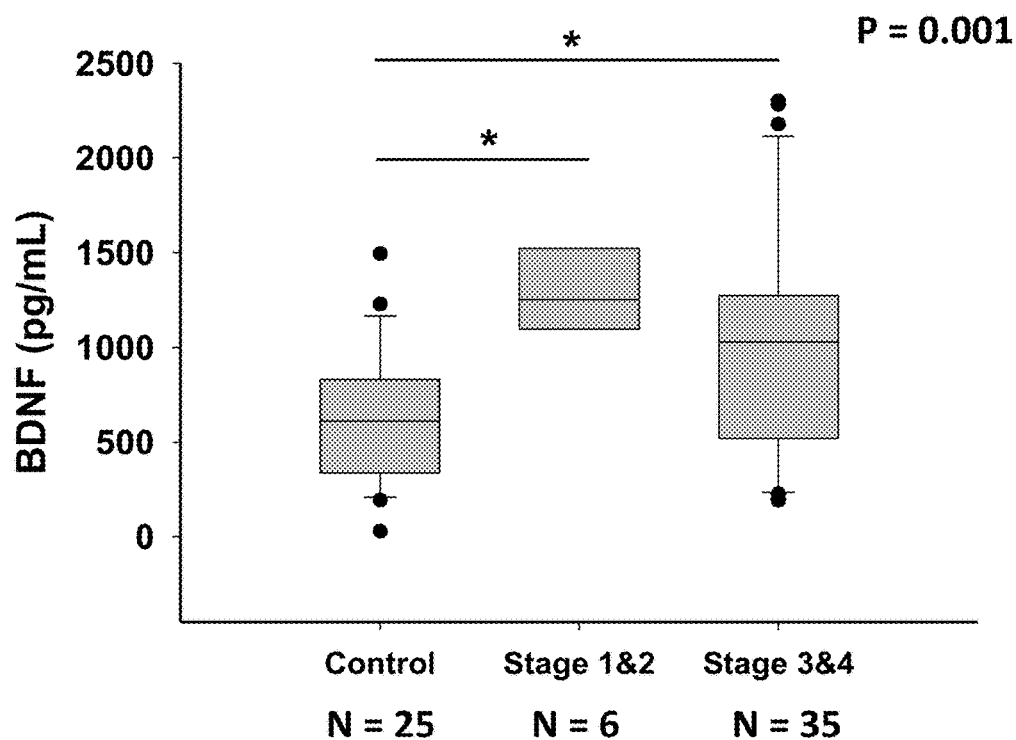
FIG. 2 graphically illustrates that total plasma BDNF concentration is significantly higher in women at any stage of endometriosis vs. controls.

Results:

Circulating concentrations of BDNF were found to be higher in the plasma of women with endometriosis vs. symptomatic and asymptomatic controls as shown in FIG. 1. The data included only women not receiving hormone treatment for endometriosis. The control group was composed of 36% symptomatic and 64% asymptomatic mammals. The endometriosis group included mammals in endometriosis stages I and II (15%) and stages III and IV (85%). Comparisons were made by t-test. Mean total plasma BDNF concentrations were significantly higher in women with stage I and II endometriosis, and with stages III and IV endometriosis vs. controls (see FIG. 2). Data were compared by one-way ANOVA and appropriate posthoc comparison test.

Figure 3:
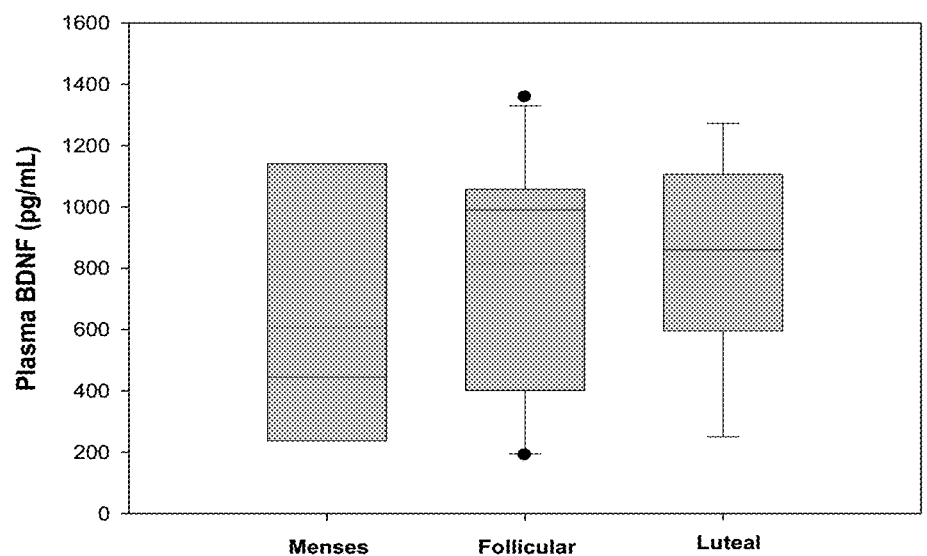
FIG. 3 graphically demonstrates that plasma total BDNF concentration is similar across the menstrual cycle.

A comparison of plasma total BDNF concentrations across the menstrual cycle (menses, follicular and luteal) indicated that the concentration was similar during the entire cycle (see FIG. 3).

Figure 4:
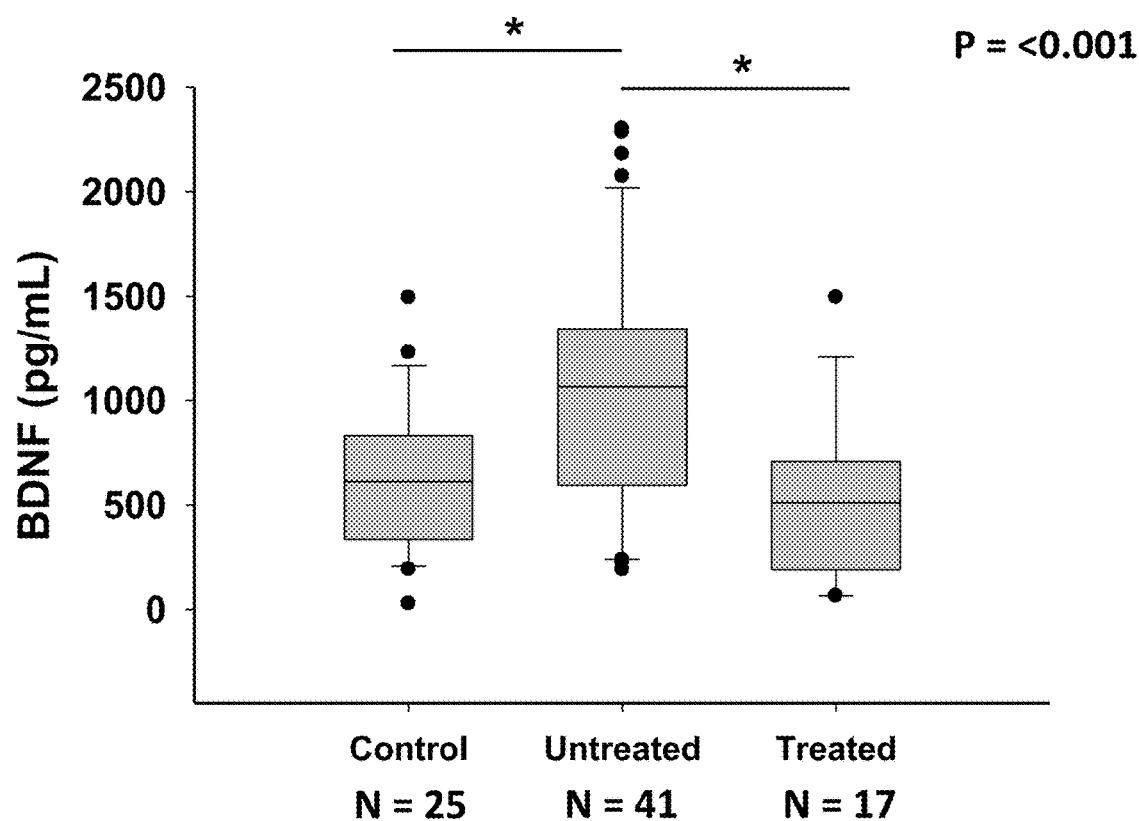
FIG. 4 compares plasma BDNF concentration in women with endometriosis prior to treatment (untreated), and subsequent to treatment (treated)
Figure 5:
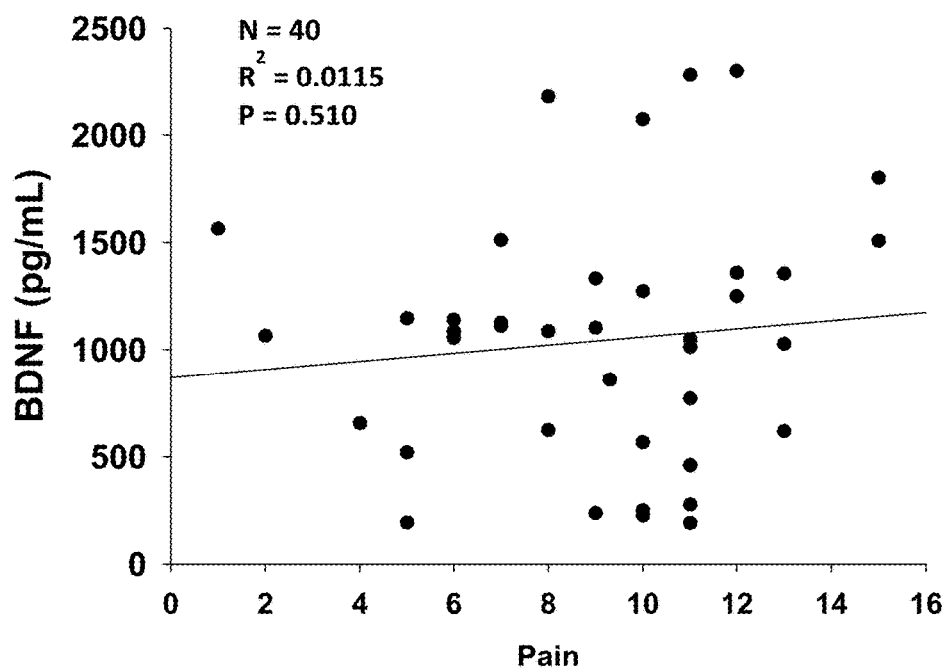
FIG. 5 illustrates the relationship between plasma BDNF concentrations and pain scores in mammals with untreated endometriosis.

Plasma BDNF concentrations were compared in controls (women without endometriosis), women with endometriosis prior to ovarian suppression treatment (untreated), and women with endometriosis who were being treated for their disease with ovarian suppressing hormone treatments (oral contraceptives or Lupron). These results showed that treatment of endometriosis resulted in a decrease in plasma BDNF to levels comparable to control levels (FIG. 4). Data were compared by one-way ANOVA and appropriate post-hoc test.

A comparison of plasma BDNF concentrations against pain was also conducted. BDNF plasma concentrations were found to be positively correlated with pain scores, which is a primary presenting complaint of mammals with endometriosis. Linear Regression performed using pain as the dependent variable and plasma BDNF concentration as the independent variable.

Example 2—mBDNF and Ntrk2 Expression Linked to Endometriosis

Western blot analysis of BDNF and Ntrk2 from human endometrium of healthy women was conducted. Extracted protein (60 mg) from human endometrium was run on a 4-20% gradient gel (Thermo-Scientific) at 150 V for 50 minutes. Protein was transferred to PVDF membrane (VWR International, Mississauga, ON, Canada) at 40 V for 90 minutes. Blots were blocked for 1 hour at room temperature with 5% skim milk/TBS-T, and subsequently probed with 1:1000 rabbit anti-BDNF (Abcam) or 1:1000 rabbit anti-Ntrk2 (Abcam), overnight at 4° C. Anti-Rabbit-ECL secondary (GE, Mississauga, ON, Canada) at a concentration of 1:5000 was applied for 1 hour at room temperature, blots were briefly washed in TBS-T and TBS, then incubated with ECL substrate (Thermo-Scientific) for 5 minutes. Exposures were performed using x-ray film (Thermo-Scientific), and the exposure times were 60, and 45 minutes for BDNF and Ntrk2 respectively. Mouse brain was used as a positive control, and beta-actin as a loading control.

Figure 6:
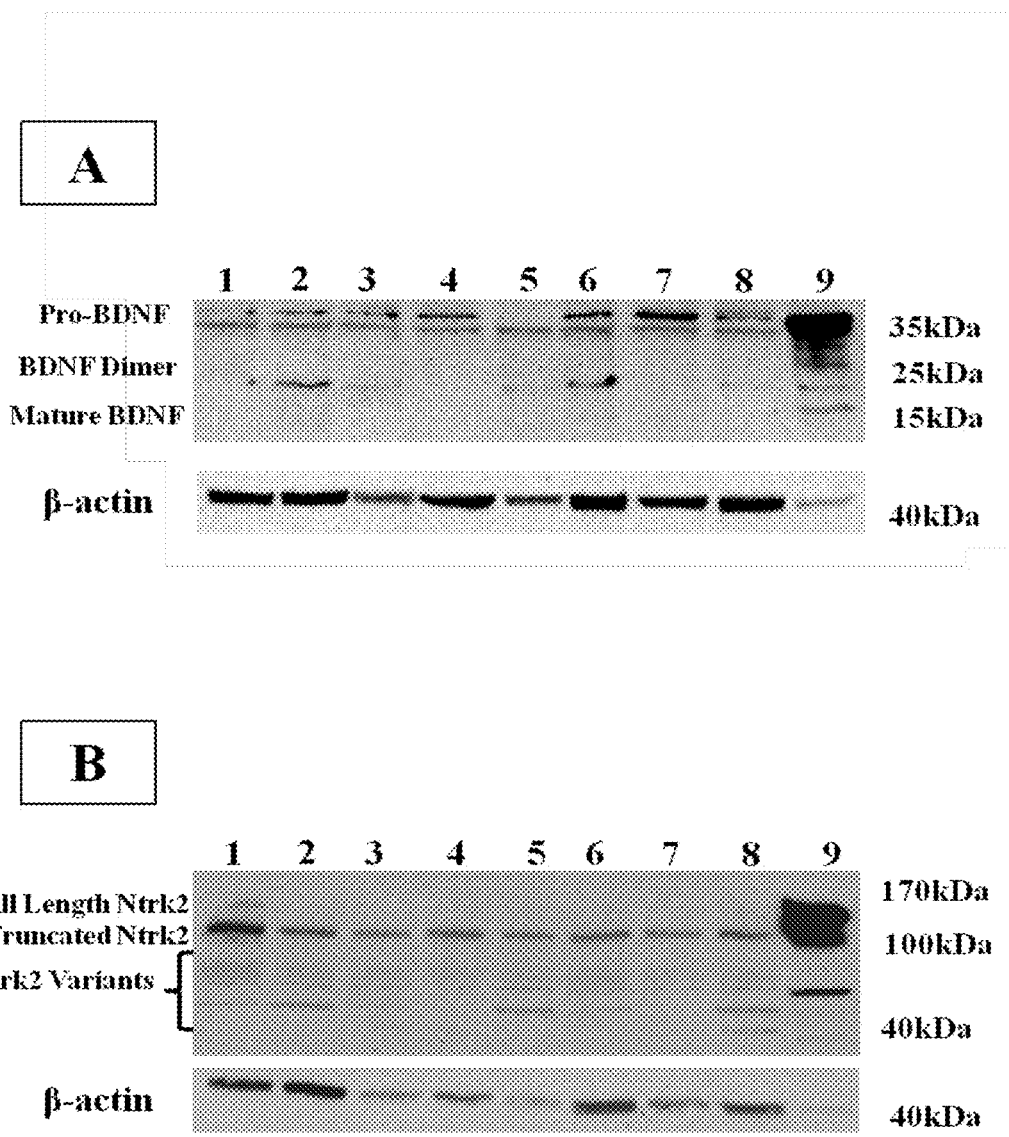
FIG. 6 shows the results of Western blot analysis of human endometrium from healthy women illustrating that pro-BDNF is the dominant form present (A), and that truncated Ntrk2 is the dominant isoform present (B)

BDNF in the Human Uterus.

pro-BDNF (35 kDa) was found to be the dominant form present whereas mBDNF was not detectable (FIG. 6A). A similar analysis was conducted on endometrium from women with endometriosis and the mBDNF form was overexpressed as compared to the other forms vs. controls.

Ntrk2 Expression in the Human Uterus.

Figure 7:
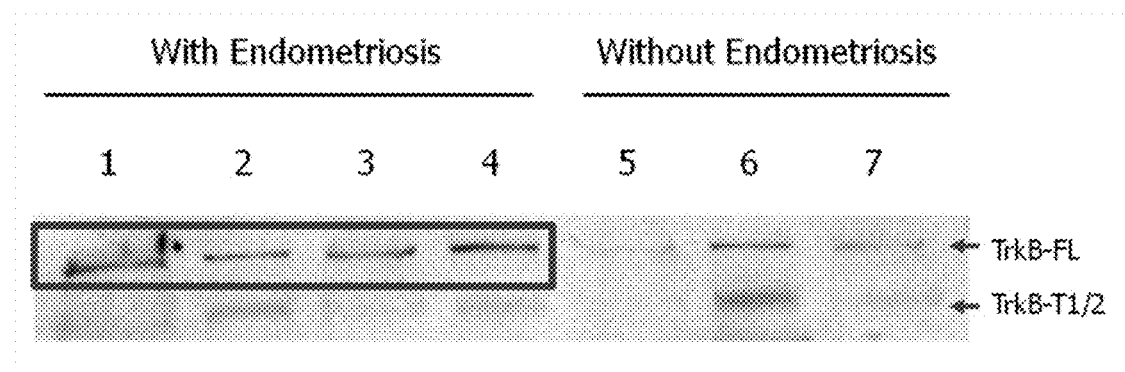
FIG. 7 shows a Western blot analysis of endometrium obtained from women with endometriosis vs. healthy controls showing that the full-length (FL) variant of Ntrk2 is overexpressed in endometriosis.

The truncated form of Ntrk2 was found to be the dominant isoform present whereas the full-length isoform was low to non-detectable (FIG. 6B). A similar analysis was conducted on endometrium from women with endometriosis and the full-length (FL) variant of Ntrk2 was overexpressed compared to a truncated (T1/2) variant of Ntrk2x vs. controls (FIG. 7).

Example 3—Determination of BDNF and Ntrk2 Expression by PCR

RNA from mouse, rat, human, pig, and horse was reverse transcribed using the iScript cDNA synthesis kit (Bio-Rad), according to kit protocol. PCR primers were designed using human GenBank sequences for BDNF mRNA (NM_001143809.1) and Ntrk2 mRNA (NM_006180.3). Primers were designed against a 300 bp span within the coding region of the gene, and whenever possible were designed to span an intron. Primer3 software (http://frodo.wi.mit.edu/primer3/) was used for primer design and primers were tested for hairpins, self-dimers, and heterodimers using OligoAnalyzer 3.1 (http://www.idtdna.com/analyzer/applications/oligoanalyzer/). Primer sequences for BDNF were (Forward: GAGCTGAGCGTGTGTGACAG (SEQ ID NO:9), Reverse: CTTATGAATCGCCAGCCAAT (SEQ ID NO:10)), and for Ntrk2 (For ward: CAATTGTG-GTTTGCCATCTG (SEQ ID NO:11), Reverse: TGCAAAATGCACAGTGAGGT (SEQ ID NO:12)). Primers were ordered from Mobix Laboratory (McMaster University, Hamilton, ON, Canada), and diluted to a working concentration of 10 pmol/ml with DNase/RNase free water. cDNA for 3 animals per group was pooled and used to isolate BDNF and Ntrk2 transcripts. Real-Time PCR was performed in triplicate in a 10 ml reaction volume (2 ml pooled cDNA, 5 ml SYBR Green Master Mix (Qiagen), 1 ml forward primer, 1 ml reverse primer, and 1 ml RNase/DNase free water) using the capillary-based LightCycler (Roche Diagnostics, Laval, QC, Canada). The program was denaturation: 95° C. for 15 min; amplification: 55 cycles: 95° C. for 10 s, 56° C. for 5 s, 72° C. for 20 s; melting curve: 70-95° C. at a rate of 0.1° C. per second. Amplification and melt curves were analyzed for each species using the LightCycler software (Roche Diagnostics). PCR products were collected, and sent for sequencing (Laboratory Services, University of Guelph).

Both primer pairs isolated specific products which were verified by sequencing in all species (human, mouse, rat, and horse).

Example 4

Several studies have indicated that estradiol ($E_2$) treatment alters the expression of Ntrk2 and/or its ligand, BDNF, in neural tissue. To determine if BDNF expression was altered in the uterus, the following study was conducted.

BDNF transcripts were measured in the murine uterus of ovariectomized mice by Real Time PCR and relative expression quantified in mice receiving saline (Control (n=4)), estradiol primed then estradiol (E2 (n=6)), estradiol primed then progesterone (P4 (n=6)), estradiol primed then estradiol+progesterone ($E_2+P_4$ (n=6)), or estradiol primed then saline (Saline (n=4)).

| Group | Day 1 | Day 2 | Day 3 | Day 4 | Day 5 | Day 6 | Day 7 | Day 8 | Day 9 |
|---|---|---|---|---|---|---|---|---|---|
| Control | Saline | Saline | Saline | None | None | Saline | Saline | Saline | Saline |
| E2 | $E_2$ | $E_2$ | $E_2$ | None | None | $E_2$ | $E_2$ | $E_2$ | $E_2$ |
| P4 | $E_2$ | $E_2$ | $E_2$ | None | None | $P_4$ | $P_4$ | $P_4$ | $P_4$ |
| E2&P4 | $E_2$ | $E_2$ | $E_2$ | None | None | $E_2+P_4$ | $E_2+P_4$ | $E_2+P_4$ | $E_2+P_4$ |
| Saline | $E_2$ | $E_2$ | $E_2$ | None | None | Saline | Saline | Saline | Saline |

Figure 8:
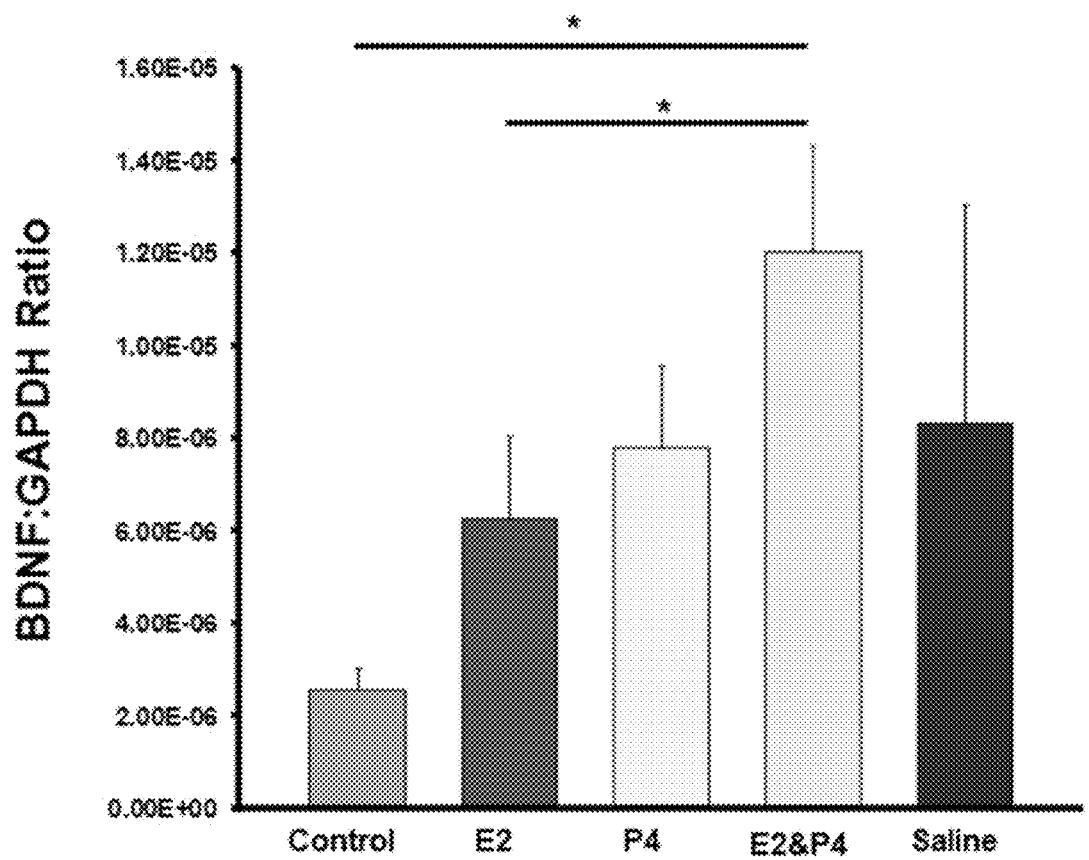
FIG. 8 illustrates BDNF transcript expression in the murine uterus in mice receiving saline (Control (n=4)), estradiol primed then estradiol (E2 (n=6)), estradiol primed then progesterone (P4 (n=6)), estradiol primed then estradiol+progesterone ($E_2+P_4$ (n=6)), or estradiol primed then saline (Saline (n=4))

BDNF expression was significantly increased in the uterus of ovariectomized mice treated with $E_2$ and progesterone ($P_4$), an effect that was further enhanced by co-treatment with $E_2$ and $P_4$ (FIG. 8).

---

The invention claimed is:

1. A method of diagnosing endometriosis in a human comprising:
   obtaining a fluid sample from the human;
   detecting the expression level of circulating BDNF in the fluid sample and detecting binding between the BDNF and an anti-BDNF antibody;
   detecting the expression level of full-length Ntrk2 in the fluid sample and detecting binding between full-length Ntrk2 and a full-length Ntrk2-specific reactant; and
   diagnosing the human with endometriosis when the circulating BDNF and Ntrk2 expression levels are both elevated by at least 10% as compared to their respective controls.

2. The method of claim 1, wherein the fluid sample is selected from the group consisting of blood, serum, plasma, urine, and peritoneal fluid.

3. The method of claim 1, wherein the BDNF and Ntrk2 control levels are the normal expression levels of each in a human without endometriosis.

4. The method of claim 1, wherein the BDNF and Ntrk2 control levels are the expression levels of a housekeeping gene that is not associated with endometriosis and encodes a protein that maintains a fixed expression level in the human.

5. The method of claim 1, wherein the control level of BDNF is 100-500 pg/ml.

6. The method of claim 1, wherein the BDNF is total plasma BDNF.

7. The method of claim 1, wherein the BDNF is mBDNF.

8. The method of claim 1, wherein the human is diagnosed with endometriosis when BDNF and Ntrk2 expression levels are elevated by at least 20%.

9. A method of monitoring a human following treatment of endometriosis comprising:
   obtaining a fluid sample from the human;
   detecting the expression level of circulating BDNF in a fluid sample and detecting binding between the BDNF and an anti-BDNF antibody; and
   determining that the human is responding to treatment when the circulating BDNF expression level is reduced by at least 10% in comparison to a pre-treatment BDNF control level.

10. A method of detecting circulating BDNF in a human comprising:
    obtaining a fluid sample from the human; and
    detecting whether BDNF is present in the sample by contacting the fluid sample with an anti-BDNF antibody and detecting binding between the BDNF and the anti-BDNF antibody.

11. The method of claim 10, wherein the fluid sample is selected from the group consisting of blood, serum, plasma, urine, and peritoneal fluid.

* * * * *

SEQUENCE LISTING

```
<160> NUMBER OF SEQ ID NOS: 12

<210> SEQ ID NO 1
<211> LENGTH: 72
<212> TYPE: PRT
<213> ORGANISM: Homo sapiens

<400> SEQUENCE: 1

Ala Val Asp Met Ser Gly Gly Thr Val Thr Val Leu Glu Lys Val Pro
1               5                   10                  15

Val Ser Lys Gly Gln Leu Lys Gln Tyr Phe Tyr Glu Thr Lys Cys Asn
            20                  25                  30

Pro Met Gly Tyr Thr Lys Glu Gly Cys Arg Gly Ile Asp Lys Arg His
        35                  40                  45

Trp Asn Ser Gln Cys Arg Thr Thr Gln Ser Tyr Val Arg Ala Leu Thr
50                  55                  60

Met Asp Ser Lys Lys Arg Ile Gly
65                  70

<210> SEQ ID NO 2
<211> LENGTH: 70
<212> TYPE: PRT
<213> ORGANISM: Homo sapiens

<400> SEQUENCE: 2

Ser Ile Thr Leu Ser Cys Ser Val Ala Gly Asp Pro Val Pro Asn Met
1               5                   10                  15

Tyr Trp Asp Val Gly Asn Leu Val Ser Lys His Met Asn Glu Thr Ser
            20                  25                  30

His Thr Gln Gly Ser Leu Arg Ile Thr Asn Ile Ser Ser Asp Asp Ser
        35                  40                  45

Gly Lys Gln Ile Ser Cys Val Ala Glu Asn Leu Val Gly Glu Asp Gln
    50                  55                  60

Asp Ser Val Asn Leu Thr
65                  70

<210> SEQ ID NO 3
<211> LENGTH: 71
<212> TYPE: PRT
<213> ORGANISM: Mus musculus

<400> SEQUENCE: 3

Lys Ser Val Thr Leu Ser Cys Ser Val Gly Gly Asp Pro Leu Pro Thr
1               5                   10                  15
```

```
Leu Tyr Trp Asp Val Gly Asn Leu Val Ser Lys His Met Asn Glu Thr
            20                  25                  30

Ser His Thr Gln Gly Ser Leu Arg Ile Thr Asn Ile Ser Ser Asp Asp
        35                  40                  45

Ser Gly Lys Gln Ile Ser Cys Val Ala Glu Asn Leu Val Gly Glu Asp
    50                  55                  60

Gln Asp Ser Val Asn Leu Thr
65                  70

<210> SEQ ID NO 4
<211> LENGTH: 70
<212> TYPE: PRT
<213> ORGANISM: Rattus norvegicus

<400> SEQUENCE: 4

Ser Val Thr Ile Ser Cys Ser Val Gly Gly Asp Pro Leu Pro Thr Leu
1               5                   10                  15

Tyr Trp Asp Val Gly Asn Leu Val Ser Lys His Met Asn Glu Thr Ser
            20                  25                  30

His Thr Gln Gly Ser Leu Arg Ile Thr Asn Ile Ser Ser Asp Asp Ser
        35                  40                  45

Gly Lys Gln Ile Ser Cys Val Ala Glu Asn Leu Val Gly Glu Asp Gln
    50                  55                  60

Asp Ser Val Asn Leu Thr
65                  70

<210> SEQ ID NO 5
<211> LENGTH: 219
<212> TYPE: DNA
<213> ORGANISM: Homo sapiens

<400> SEQUENCE: 5
tgcagtggac atgtcgggcg ggacggtcac agtccttgaa aaggtccctg tatcaaaagg    60
ccaactgaag caatacttct acgagaccaa gtgcaatccc atgggttaca caaaagaagg   120
ctgcaggggc atagacaaaa ggcattggaa ctcccagtgc cgaactaccc agtcgtacgt   180
gcgggccctt accatggata gcaaaaagag aattggctg                          219

<210> SEQ ID NO 6
<211> LENGTH: 216
<212> TYPE: DNA
<213> ORGANISM: Mus musculus

<400> SEQUENCE: 6
tgcagtggac atgtctggcg ggacggtcac agtcctagag aaagtcccgg tatccaaagg    60
ccaactgaag cagtatttct acgagaccaa gtgtaatccc atgggttaca ccaaggaagg   120
ctgcaggggc atagacaaaa ggcactggaa ctcgcaatgc cgaactaccc aatcgtatgt   180
tcgggccctt actatggata gcaaaaagag aattgg                             216

<210> SEQ ID NO 7
<211> LENGTH: 219
<212> TYPE: DNA
<213> ORGANISM: Rattus norvegicus

<400> SEQUENCE: 7
tgcagtggac atgtccggtg ggacggtcac agtcctggag aaagtcccgg tatcaaaagg    60
ccaactgaag caatatttct acgagaccaa gtgtaatccc atgggttaca cgaaggaagg   120
```

```
ctgcagggc atagacaaaa ggcactggaa ctcgcaatgc cgaactaccc aatcgtatgt    180 tcgggcccctt actatggata gcaaaaagag aattggctg                         219
```

<210> SEQ ID NO 8
<211> LENGTH: 210
<212> TYPE: DNA
<213> ORGANISM: Homo sapiens

<400> SEQUENCE: 8

```
gtctatcaca ttatcctgta gtgtggcagg tgatccggtt cctaatatgt attgggatgt    60
tggtaacctg gtttccaaac atatgaatga acaagccac acacagggct ccttaaggat    120
aactaacatt tcatccgatg acagtgggaa gcagatctct tgtgtggcgg aaaatcttgt   180
aggagaagat caagattctg tcaacctcac                                    210
```

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9

```
gagctgagcg tgtgtgacag                                               20
```

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10

```
cttatgaatc gccagccaat                                               20
```

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11

```
caattgtggt ttgccatctg                                               20
```

<210> SEQ ID NO 12
<211> LENGTH: 20
<212> TYPE: DNA
<213> ORGANISM: Artificial
<220> FEATURE:
<223> OTHER INFORMATION: priimer

<400> SEQUENCE: 12

```
tgcaaaatgc acagtgaggt                                               20
```